(12) United States Patent
McKay et al.

(10) Patent No.: US 8,048,857 B2
(45) Date of Patent: Nov. 1, 2011

(54) FLOWABLE CARRIER COMPOSITIONS AND METHODS OF USE

(75) Inventors: William F. McKay, Memphis, TN (US); Steven M. Peckham, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 202 days.

(21) Appl. No.: 11/612,853

(22) Filed: Dec. 19, 2006

(65) Prior Publication Data
US 2008/0147065 A1  Jun. 19, 2008

(51) Int. Cl.
*A61K 38/18* (2006.01)

(52) U.S. Cl. ......... 514/16.7; 514/1.1; 514/8.8; 424/422; 424/423

(58) Field of Classification Search .................. None
See application file for complete search history.

(56) References Cited

U.S. PATENT DOCUMENTS

| | | |
|---|---|---|
| 3,944,655 A | 3/1976 | Levin et al. |
| 4,394,370 A | 7/1983 | Jefferies |
| 4,472,840 A | 9/1984 | Jefferies |
| 4,563,489 A | 1/1986 | Urist |
| 4,623,553 A | 11/1986 | Ries et al. |
| 4,698,326 A | 10/1987 | Sauk et al. |
| 4,755,593 A | 7/1988 | Lauren |
| 4,780,450 A | 10/1988 | Sauk et al. |
| 4,865,602 A | 9/1989 | Smestad et al. |
| 4,963,145 A | 10/1990 | Takagi et al. |
| 5,043,426 A | 8/1991 | Goldstein |
| 5,231,169 A | 7/1993 | Constantz et al. |
| 5,238,491 A | 8/1993 | Sugihara et al. |
| 5,246,457 A | 9/1993 | Piez et al. |
| 5,320,844 A | 6/1994 | Liu |
| 5,425,770 A | 6/1995 | Piez et al. |
| 5,455,231 A | 10/1995 | Constantz et al. |
| 5,508,267 A | 4/1996 | Czernuszka et al. |
| 5,531,791 A | 7/1996 | Wolfinbarger, Jr. |
| 5,532,217 A | 7/1996 | Silver et al. |
| 5,674,292 A | 10/1997 | Tucker et al. |
| 5,707,962 A | 1/1998 | Chen et al. |
| 5,739,286 A | 4/1998 | Silver et al. |
| 5,776,193 A | 7/1998 | Kwan et al. |
| 5,916,870 A | 6/1999 | Lee et al. |
| 6,013,856 A | 1/2000 | Tuckert et al. |

(Continued)

FOREIGN PATENT DOCUMENTS

EP  1454640 A2  9/2004

(Continued)

OTHER PUBLICATIONS

Haid, Jr. et al, Posterior lumbar interbody fusion using recombinant human bone morphogenetic protein type 2 with cylindrical interbody cages; The Spine Journal, vol. 4, No. 5, pp. 527-538 (2004).

(Continued)

*Primary Examiner* — Elizabeth C Kemmerer

(57) ABSTRACT

A composition is provided for faster bone repair and early orthopedic implant fixation. The composition comprises an osteoinductive or osteopromotive biological factor embedded in a carrier slurry. The slurry is prepared by wetting a biodegradable polymer and calcium phosphate particles with a biocompatible fluid. The composition may be applied to the site of the bone fracture, to an orthopedic implant or to both during the surgical procedure. The composition utilizes low dosages of the biological factor and, therefore, is cost effective to be used routinely.

26 Claims, 5 Drawing Sheets

U.S. PATENT DOCUMENTS

| | | | |
|---|---|---|---|
| 6,028,242 | A | 2/2000 | Tucker et al. |
| 6,180,606 | B1 | 1/2001 | Chen et al. |
| 6,187,047 | B1 | 2/2001 | Kwan et al. |
| 6,300,315 | B1 | 10/2001 | Liu |
| 6,311,690 | B1 | 11/2001 | Jefferies |
| 6,379,962 | B1 | 4/2002 | Holy et al. |
| 6,417,166 | B2 | 7/2002 | Liu |
| 6,461,630 | B1 | 10/2002 | Tucker et al. |
| 6,485,751 | B1 | 11/2002 | Wang |
| 6,504,079 | B2 | 1/2003 | Tucker et al. |
| 6,764,517 | B2 | 7/2004 | Yamamoto et al. |
| 6,902,584 | B2 | 6/2005 | Kwan et al. |
| 6,969,523 | B1 | 11/2005 | Mattern et al. |
| 2001/0014830 | A1 | 8/2001 | Kwan et al. |
| 2001/0014831 | A1* | 8/2001 | Scarborough .............. 623/23.51 |
| 2001/0016703 | A1* | 8/2001 | Wironen et al. ................ 604/89 |
| 2002/0055143 | A1 | 5/2002 | Bell et al. |
| 2002/0183855 | A1 | 12/2002 | Yamamoto et al. |
| 2003/0031698 | A1 | 2/2003 | Roeder et al. |
| 2004/0029699 | A1* | 2/2004 | Lemaitre et al. .................. 501/1 |
| 2004/0033249 | A1 | 2/2004 | Sewing et al. |
| 2004/0109937 | A1 | 6/2004 | Jennissen et al. |
| 2004/0138758 | A1* | 7/2004 | Evans et al. ................ 623/23.51 |
| 2004/0220680 | A1 | 11/2004 | Yamamoto et al. |
| 2005/0020506 | A1 | 1/2005 | Drapeau et al. |
| 2005/0064007 | A1 | 3/2005 | Steinemann et al. |
| 2005/0152881 | A1* | 7/2005 | Mills et al. ................... 424/93.7 |
| 2005/0217538 | A1 | 10/2005 | Reinstorf et al. |
| 2006/0039947 | A1 | 2/2006 | Schmidmaier et al. |
| 2011/0002894 | A1* | 1/2011 | Chaudhry et al. ........... 424/93.7 |

FOREIGN PATENT DOCUMENTS

| | | |
|---|---|---|
| JP | 2002210002 A | 7/2002 |
| WO | WO0047114 A | 8/2000 |
| WO | WO0128602 A1 | 4/2001 |
| WO | WO02058755 A2 | 8/2002 |
| WO | WO2005025595 A2 | 3/2005 |
| WO | WO2008016891 A1 | 2/2008 |

OTHER PUBLICATIONS

Lind et al., Effect of osteogenic protein 1/collagen composite combined with impacted allograft around hydroxyapatite-coated titanium alloy implants is moderate; J. Biomed Mater Res., 1:89-98 (Apr. 2001).

International Search Report PCT/US2007/087117 mailed Jul. 11, 2008.

* cited by examiner

FLOWABLE CARRIER COMPOSITIONS AND METHODS OF USE

FIELD OF THE INVENTION

The present invention relates to products and related methods for orthopedic implants. More particularly, the present invention discloses using a biological factor in a carrier slurry.

BACKGROUND OF THE INVENTION

The human skeleton is made up of 206 bones. The bones, also called osseous tissue, are a type of hard endoskeletal connective tissue that supports body structures, protects internal organs, and (in conjunction with muscles) facilitates movement. Unfortunately, bones are subject to fracturing as a result of physical trauma or certain medical conditions that weaken the bones, such as osteoporosis or certain types of cancer. Although fractured bones can heal by natural processes, it may sometimes be necessary to reinforce or stabilize the bones with metal implants during the healing process.

More importantly, replacing a joint affected by osteoarthritis ("OA") with a prosthetic device is a common procedure. OA is a degenerative joint disease characterized by progressive break down of the cartilage matrix. Cartilage is the part of the joint that cushions the ends of the bones and allows easy movement of joints. It also absorbs energy from the shock of physical movement. The breakdown of cartilage causes the bones to rub against each other, causing stiffness, pain and loss of movement in the joint. OA affects approximately 21 million Americans a year, accounting for 25% of visits to primary care physicians. It is estimated that 80% of the population will have radiographic evidence of OA by age 65 with more than 60% of those exhibiting symptoms.

If the joint does not respond to conservative treatment such as medication, weight loss, activity restriction, and use of walking aids such as a cane, joint replacement with a prosthetic device is considered appropriate. The most common joints to be replaced are knees and hips. About 435,000 Americans have a hip or knee replaced each year. Research has shown that joint replacement can help even older patients to move around and feel better. For a joint replacement to succeed, the prosthetic replacements require rapid bone ingrowth in them to stabilize the implant and allow the patient to resume the normal activities of daily living.

The mechanical disturbance of the bone after fracture or during surgery may, however, delay its repair and regeneration resulting in transient instability of the implant. In addition, it may lead to a fibrous tissue interposition between the bone and the implant which may lead to loosening of the implant. Loosening of the joint is the most common cause of failure in hip joints that are not infected. This may require another joint replacement surgery in about 12% of patients within a 15-year period following the first procedure. Thus, younger patients may need to have the same damaged joint replaced more than once.

Prior attempts have been made to modify the surface of orthopedic implants with biological substances to promote faster bone repair and to facilitate early implant fixation. Because in these prior art attempts the implant is coated during the manufacturing process, pre-application of a biologically active substance at the time of manufacture increases the cost of the surgical procedure because excessive amounts of the expensive biological factor are needed during the manufacturing process and to ensure it's long term sterility and stability. In addition, pre-applying the biological substance at the time of manufacture also does not allow a surgeon to customize the amount of a biologically active substance applied to the implant for a particular procedure.

Accordingly, there is still a need in the art for a intraoperative, user-friendly, flexible, and relatively inexpensive method to facilitate early implant fixation.

SUMMARY OF THE INVENTION

In one aspect, a composition is provided that comprises an effective amount of a biological factor and a carrier slurry, which may facilitate early implant fixation. The biological factor may be selected from substances that stimulate and induce bone growth such as, for example, Bone Morphogenetic Proteins, Growth Differentiation Factors, or Statins. Certain embodiments permit low dosages of the biological factor. As a result, the composition of the current invention may be cost effective and can be used routinely.

The carrier slurry is used to ensure even distribution of the biological factor over the bone or the implant surface and to keep the biological factor at the injury site for a desired period of time. The carrier slurry comprises a biocompatible fluid, a biodegradable polymer and a calcium phosphate compound. The slurry may be formed by wetting a dry mixture of the biodegradable polymer and the calcium phosphate compound with, for example, a biocompatible fluid.

Another aspect provides a method for using a composition described above to promote bone repair and regeneration. The method comprises preparing the composition described above, applying the composition to the bone surface in or around an injury, and stabilizing the bone to prevent further injury. The composition can be applied to the bone by either applying the composition directly to the bone or applying the composition to the implant before insertion of the implant into the bone.

In yet another aspect, a medical kit for practicing the methods described above is provided. The kit includes a biological factor, a biodegradable polymer, a calcium phosphate compound, a biocompatible fluid, an applicator for applying the biological factor and a carrier slurry resulting after wetting the biodegradable polymer and the calcium phosphate compound with the biocompatible fluid to the site of the bone repair or to an orthopedic implant, and a set of instructions on how to use the kit of the present invention. The biological factor may be provided separately from the biocompatible fluid or diluted in the biological fluid. Similarly, the biodegradable polymer and the calcium phosphate particles may be provided separately or pre-mixed.

The present invention, including all its features and advantages, will become more apparent from the following detailed description.

DETAILED DESCRIPTION

Figure 1:
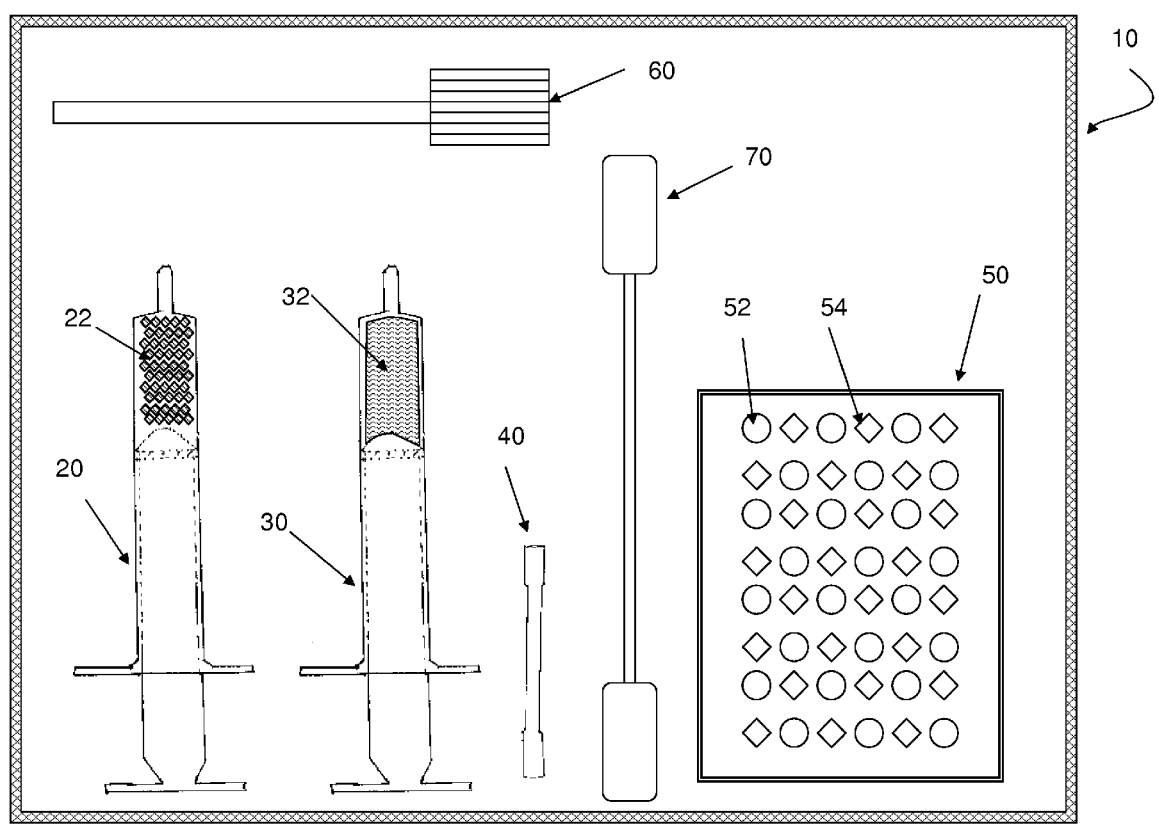
FIG. 1 depicts one embodiment of a medical kit.

One aspect provides a composition for promoting bone formation to stabilize an orthopedic implant, the composition comprising an effective amount of a biological factor embedded in a carrier slurry. The carrier slurry includes a biocompatible fluid, a biodegradable polymer and a calcium phosphate compound.

A biological factor refers to an osteoinductive substance that stimulates or induces bone growth, or an osteopromotive substance that facilitates bone growth. The term "osteoinductive substance" means a substance with the ability to stimulate the proliferation and differentiation of pluripotent mesenchymal stem cells (MSCs). Osteoinduction can be stimulated by osteogenic growth factors, although some ECM proteins can also drive progenitor cells toward the osteogenic phenotype. The term "osteopromotive substance" means a substance with the ability to stimulate the biochemical process of bone formation.

Example biological factors include, but are not limited to, Bone Morphogenetic Proteins (BMPs), including BMP-2, BMP-3, BMP-4, BMP-5, BMP-6, BMP-7, BMP-8, BMP-9, BMP-10, BMP-11, BMP-12, BMP-13, BMP-14, BMP-15, BMP-16, BMP-17, and BMP-18; Osteogenic proteins; Vascular Endothelial Growth Factors (VEGFs), including VEGF-A, VEGF-B, VEGF-C, VEGF-D and VEGF-E; Connective Tissue Growth Factors (CTGFs), including CTGF-1, CTGF-2, and CTGF-3; Osteoprotegerin Transforming Growth Factor betas (TGF-βs), including TGF-β-1, TGF-β-2, and TGF-β-3, and inhibitors for tumor necrosis factor (e.g., Enbrel®). Biological factors may also include Platelet Derived Growth Factors (PDGFs), including PDGF-A, PDGF-B, PDGF-C, PDGF-D, and GDF-5; rhGDF-5; Nell-1 protein, LIM mineralization protein and peptides; insulin-related growth factor-I (IGF-I), insulin-related growth factor-II (IGF-II); fibroblast growth factor (FGF) and beta-2-microglobulin (BDGF II), as disclosed in the U.S. Pat. No. 6,630,153, which is incorporated herein by reference. The polynucleotides encoding the same may also be administered as gene therapy agents.

The biological factor may also include statins, such as lovastatin, mavastatin, pravastatin, simvastatin, compactin (mevastatin), atorvastatin, fluvastatin, simvastatin and cerivastatin. Simvastatin, mavastatin, fluvastatin and lovastatin were found to activate the promoter for BMP-2 in rodents.

The preferred biological factors are the recombinant human bone morphogenetic proteins (rhBMPs) because they are available in relatively unlimited supply and do not transmit infectious diseases. Most preferably, the bone morphogenetic protein is rhBMP-2, rhBMP-4, rhBMP-7, or heterodimers thereof.

The concentration of the biological factor in the carrier slurry may range between about 0.01 to 10 mg/cc, i.e weight of the biological factor per volume of the carrier slurry. Preferably, the concentration of the biological factor is between approximately 0.05 to 2 mg/cc, and more preferably between approximately 0.1 to 1.0 mg/cc. In certain embodiments, a relatively low dosage of the biological factor may be utilized. This low dosage may induce bone formation without any local transient bone resorption. Alternatively, a higher dosage of the biological factor may be required when slow bone growth is expected, for example, in patients with known co-morbidities such as smokers, diabetics, and those on steroids.

Biological factors such as BMPs are water-soluble, relatively low-molecular weight proteins that diffuse very easily in bodily fluids. It has been shown that a BMP delivered without a carrier does not endure more than a few hours at the deposited site. Accordingly, a carrier slurry is provided to enclose the biological factor. The term "carrier slurry" refers to a flowable biomaterial used to ensure even distribution of the biological factor over the bone or implant surface and to keep the biological factor at the injury site for the desired period of time. It may be preferable that the biological factor is released over approximately a 1 to 30 day period, and more preferably over approximately a 7 to 21 day period.

The term "flowable" in this context applies to compositions whose consistencies range from those that are deformable, e.g., those that behave like putty, to those which are runny. The viscosity of slurry in the present invention ranges from about 100 to about $1\times10^8$ centipoises. The lower viscosity compositions are especially suitable when adhesion and entry of the composition into a cancellous bone surface or an open porous textured metal implant surface is desired. Alternatively, higher viscosity compositions may be desirable where the composition is to be packed or filled, for example, into a void, defect, interbody fusion device or disc space, as such a composition may be flowable, but may also be cohesive and compression-resistant.

The carrier slurry may be formed by hydrating a dry carrier with a biocompatible fluid. The dry carrier may comprise a biodegradable polymer and a calcium phosphate compound in dry form. In preferred embodiments, the ratio of the biodegradable polymer to the calcium phosphate compound is between about 80:20 to 40:60 by weight, preferably between approximately 75:25 and 50:50. The slurry may include more than one type of biodegradable polymer or calcium phosphate. It can also include other additives such as, for example, crosslinking agents.

Preferably, the volume ratio of the biocompatible fluid to the dry carrier is between about 1:1 to 1:4. The biological factor is preferably delivered over a period of approximately 1 to 30 days, and most preferably between approximately 7 to 21 days. Accordingly, the amounts of the biodegradable polymer and the calcium phosphate compound should be sufficient so the slurry has a residence time in the body of approximately 1 to 30 days and most preferably approximately 7 to 21 days. The amount of dry carrier may also be selected based on the injury or the size of the implant to provide enough material to sufficiently cover all bone or implant surfaces, or, when applicable, to fill voids or defects in the target site.

The term "biodegradable polymer" means a synthetic or a naturally derived biodegradable, biocompatible polymer that may be absorbed (resorbed) once implanted in a living mammalian body. It may be preferable to use a natural polymer when practicing the present invention. Example natural biodegradable polymers include, but are not limited to, collagen, hyaluronic acid, fibrin glue, bone marrow, chitosan, alginate, cellulose, starches, silk, elastin, and other animal- or plant-derived polysaccharides.

Collagen is the most commonly used carrier. For example, a Type I bovine collagen may be used in the present invention. A highly purified resorbable bovine Type I collagen may preferably be composed of two formulations of collagen, that is, an insoluble fibrous collagen and a soluble collagen. The weight ratio of insoluble collagen to soluble collagen may be between approximately 30:70 and 70:30. The ratio of soluble collagen and insoluble collagen effects the viscosity of the slurry; using a higher percentage of insoluble collagen results in a thicker slurry. Preferably, the collagen in the carrier slurry is a mixture of insoluble collagen fibers and acid-soluble collagen that are prepared from bovine hides, and contain telopeptides and 10.5% to 17% nitrogen and 10.5% to 14% hydroxyproline (average percentage by mass of the collagen portion.)

Example synthetic polymers include, but are not limited to, polyethylene glycol (PEG), polyvinyl alcohol (PVA), polyorthoester (POE), polylactic acid (PLA), polyglycolic acid (PGA), polyactic-glycolic acid (PLGA) and combinations thereof.

Examples of calcium phosphate compounds include, but are not limited to, amorphous calcium phosphate, biphasic calcium phosphate, calcium phosphate, dicalcium phosphate, dicalcium phosphate dihydrate, calcium hydroxyapatite (HA), carbonated calcium hydroxyapatite, monocalcium phosphate, monocalcium phosphate monohydrate, octacalcium phosphate, tricalcium phosphate, alpha-tricalcium phosphate, beta-tricalcium phosphate (beta-TCP), tetracalcium phosphate, and combinations thereof.

By way of a non-limiting example, the calcium phosphate compound may be a combination of 15% HA and 85% beta-TCP granules. A scaffold is formed where the 15% HA is uniformly distributed through the 85% beta-TCP. HA is a slow resorbing mineral that allows time for the remodeling to occur, while the beta-TCP is a quicker resorbing material. The combination is thus optimized to balance bony in-growth and resorption of the scaffold structure. The physical structure of the resulting scaffold emulates the highly osteoconductive porous structure of human cancellous bone, allowing for long-term stability and complete resorption. Preferably, the average pore size within the granules is approximately 0.1 to 25 microns. The granules are preferably about 0.1 to 1.6 millimeters in diameter (100 to 1600 microns), and contain a 100% mineral content.

To form a slurry, a biocompatible fluid may be added to the dry carrier, that is, to a dry mixture of a biodegradable polymer and calcium phosphate compound. Examples of biocompatible fluids include, but are not limited to, water, saline solution, buffered solutions, blood, blood with thrombin, bone marrow aspirate, glycerol, or other fluids designed to allow the material to set up in situ. In preferred embodiments, the biocompatible fluid comprises buffered solutions, or blood with thrombin. Preferably, the volume ratio of the biocompatible fluid to the dry carrier is between 1:1, i.e. slurries with lower viscosities, to 1:4, i.e thick slurries. A 1:1 ratio of biocompatible fluid to dry carrier indicates that 1 ml of biocompatible fluid is used for 1 cc of dry carrier.

By way of a non-limiting example, in one specific embodiment about 4 to 6 cc of the carrier slurry is provided with the "bulk" concentration of the biological factor after mixing with the carrier slurry of between approximately 0.10 to 0.3 mg/cc. The slurry is formed by hydrating the dry carrier with between approximately 2 ml and 4 ml of the biocompatible fluid. In another embodiment, approximately 7 to 12 cc of the carrier slurry, with a "bulk" concentration of the biological factor after mixing with the carrier slurry of between approximately 0.5 to 1.0 mg/cc, is formed using between approximately 4 and 8 ml of a biocompatible fluid.

In some embodiments, where faster resorption is desired, the composition is substantially or completely not cross-linked. In other embodiments, the compositions may be cross-linked. Cross-linked compositions may last longer after implantation and may deliver the growth factor over longer periods of time, which may be beneficial for treating defects where the bone growth is slow, or for treating patients with conditions affecting bone healing rates, such as smokers or diabetics. Cross-linking is well known in the art. For example, the composition may be crosslinked chemically with a carbodiimide, glutaraldehyde or formaldehyde among others. Alternatively, the composition may be crosslinked using e-beam or gamma irradiation or ultraviolet light. Cross-linking may also be accomplished by heat via thermal crosslinking.

The invention also provides a medical kit for preparation of the combinations described above. As described above, one of the shortcomings of the prior art when attempting to modify the surface of an orthopedic implant was that the coating was applied during the manufacturing of the implant. Accordingly, a surgeon had to decide whether to buy a coated or uncoated implant before the surgery, and could not customize the amount of biological factor applied to the implant for a particular procedure. The kit of the present invention addresses these shortcomings by allowing the surgeon to apply the biological factor to the implant herself and to customize both the amount of biological factor used and where to place it on the implant.

One embodiment of the kit is shown in FIG. 1. The kit 10 may comprise a biological factor 22 in a container 20. Container 20 may be any type of sterile container used in the art. Preferably, the biological factor 22 is contained in a syringe. The amount of biological factor may range between approximately 0.01 mg and 20 mg. In different embodiments, the kit 10 may include different amounts of the biological factor 22 to better meet the requirements of a specific procedure. The amount of biological factor 22 required for a specific procedure may vary depending on the size of the implant, type of injury or health of the patient. The present invention allows a physician to choose a kit with the minimum amount of biological factor sufficient for a specific procedure. This may decrease the cost of the procedure by reducing the amount of unused biological factor that is discarded after the procedure.

In some embodiments, as shown in FIG. 1, the kit may also include a biocompatible fluid 32 in a container 30 for hydration of the biological factor 22. The volume of biocompatible fluid 32 required to form different compositions may range between approximately 1 ml and 60 ml, and more preferable between 1 ml and 20 ml. The container 30 may be any type of sterile container used in the art. For convenience of use, the biocompatible fluid 32 may also be contained in a syringe 30 that can be connected to the syringe containing the biological factor.

Figure 2:
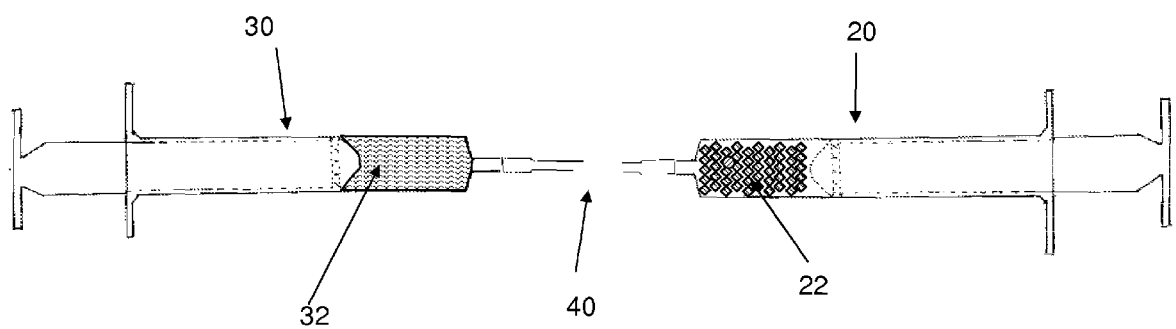
FIGS. 2 and 3 illustrate using the kit shown in FIG. 1 to create a flowable carrier matrix.
Figure 3:
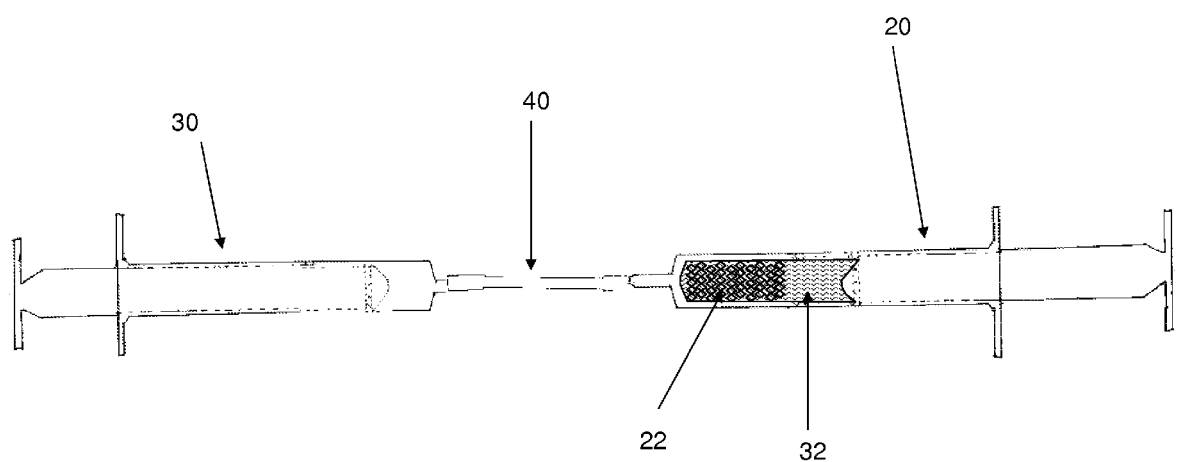

To facilitate connection of the containers 20 and 30, a connector 40 may also be provided in the kit 10. In order to dissolve the biological factor 22 in the biocompatible fluid 32, the syringe 20 and the syringe 30 may be connected using the connector 40 as shown in FIG. 2. Then, the syringe 20 containing the biological factor 22 may be loaded with a suitable amount of the biocompatible fluid 32, as shown in FIG. 3. Alternatively, the kit 10 may provide a single container containing a biocompatible fluid with a pre-dissolved biological factor.

The kit 10 may also include a biodegradable polymer 52 and calcium phosphate 54. The biodegradable polymer 52 and calcium phosphate 54 may be provided either in separate containers or, alternatively, they may be pre-mixed and provided in the same container 50, as shown in FIG. 1. In preferred embodiments, the ratio of the biodegradable polymer 52 to the calcium phosphate compound 54 is between about 80:20 to 40:60 by weight. Preferably the volume ratio of the biocompatible fluid used to hydrate the dry carrier is between 1:1 and 1:4 and the amount of dry carrier is sufficient to form between about 4 and 12 cc of the carrier slurry.

The kit 10 may include an applicator 60 that may be used for applying the slurry to bone or an implant. A spatula 70 for mixing the slurry may also be provided with the kit 10. In addition, a set of instructions (not shown) may be provided. The set of instructions preferably includes information necessary for proper use of the kit 10, such as dosage and timing of administration of the composition. Optionally, the set of instructions may also provide secondary information concerning, for example, postoperative care and observations of the patients receiving orthopedic implants coated with the composition of the present invention. A person of ordinary skill in the art will appreciate that the set of instructions can be in any suitable medium, including, without limitation, printed, video-taped, digital, and audio-recorded. In addition to English language instructions, instructions in other languages may be provided.

By way of a non-limiting example, in one specific embodiment, the kit comprises between about 0.8 and 1.2 mg of the biological factor, between about 2 and 4 ml of the biocompatible fluid, and a sufficient amount of the dry carrier to form about 4 to 6 cc of the carrier slurry. In another embodiment, the kit comprises about 3 and 6 mg of the biological factor, between about 4 and 8 ml of the biocompatible fluid, and a sufficient amount of dry carrier to form between approximately 7 and 12 cc of the carrier slurry.

Figure 4:
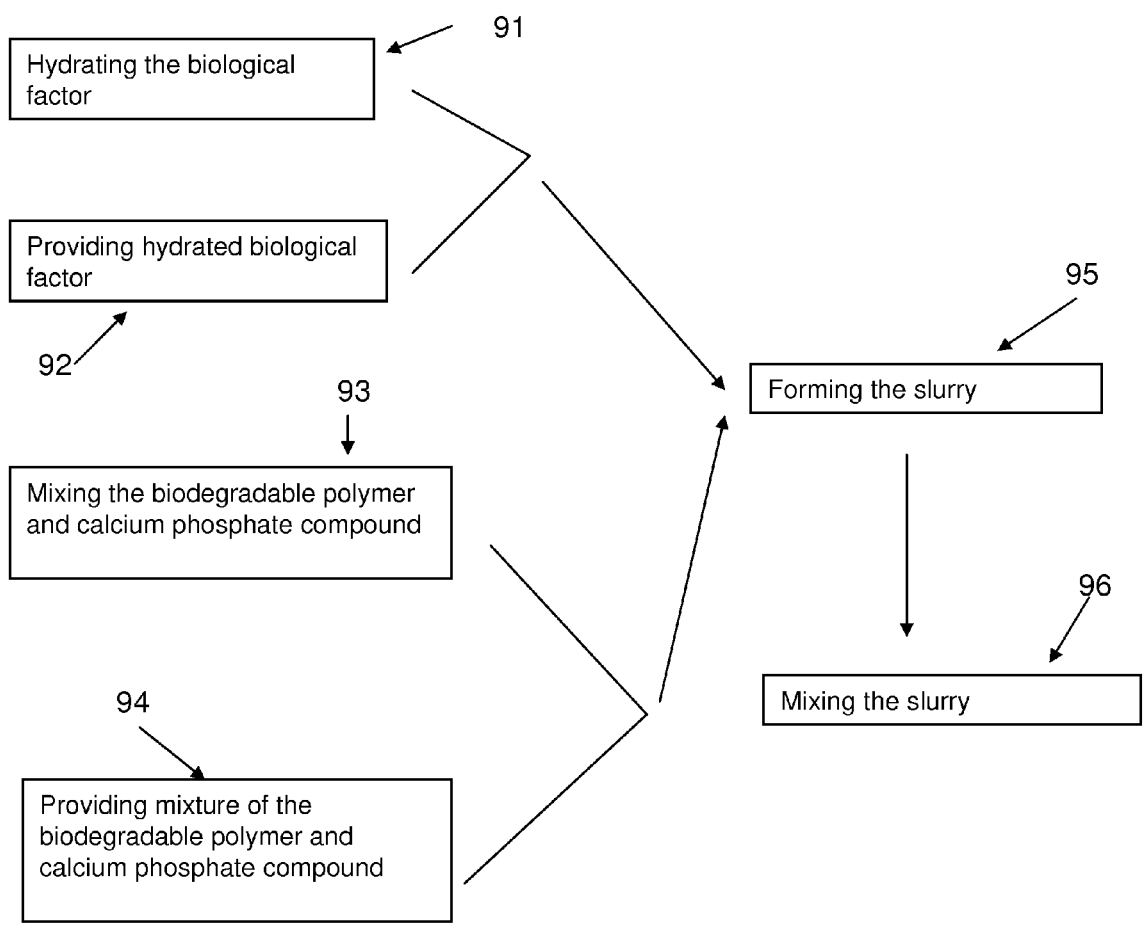
FIG. 4 and FIG. 5 provide flowcharts for preparing a carrier slurry and applying the slurry to an injured site.

The kit provides the surgeon with many of the tools necessary to practice the methods of the present invention. The first step in these methods is preparing the composition comprising a biological factor and a carrier slurry. By way of a non-limiting example, the slurry may be prepared by following the flowchart in FIG. 4.

In step 91, the biological factor is hydrated with a biocompatible fluid. One example of this step is presented in FIG. 2 and FIG. 3, and is described in detail above. Alternatively, the biological factor may be provided pre-mixed within a biocompatible fluid, as indicated by step 92.

Next, as indicated by step 93, the biodegradable polymer and calcium phosphate compound may be mixed to form a dry carrier if provided in separate containers. Alternatively, as indicated by step 94, the dry carrier may be provided pre-mixed.

In step 95, the hydrated biological factor is then added to the dry carrier to form carrier slurry. Next, in step 96, the slurry is mixed to ensure homogeneity of the slurry and an even distribution of the biological factor throughout the slurry. The slurry can be mixed manually using a spatula, or may be mixed using mechanical equipment such as blenders, homogenizers, dispersers, mixers or similar devices.

Figure 5:
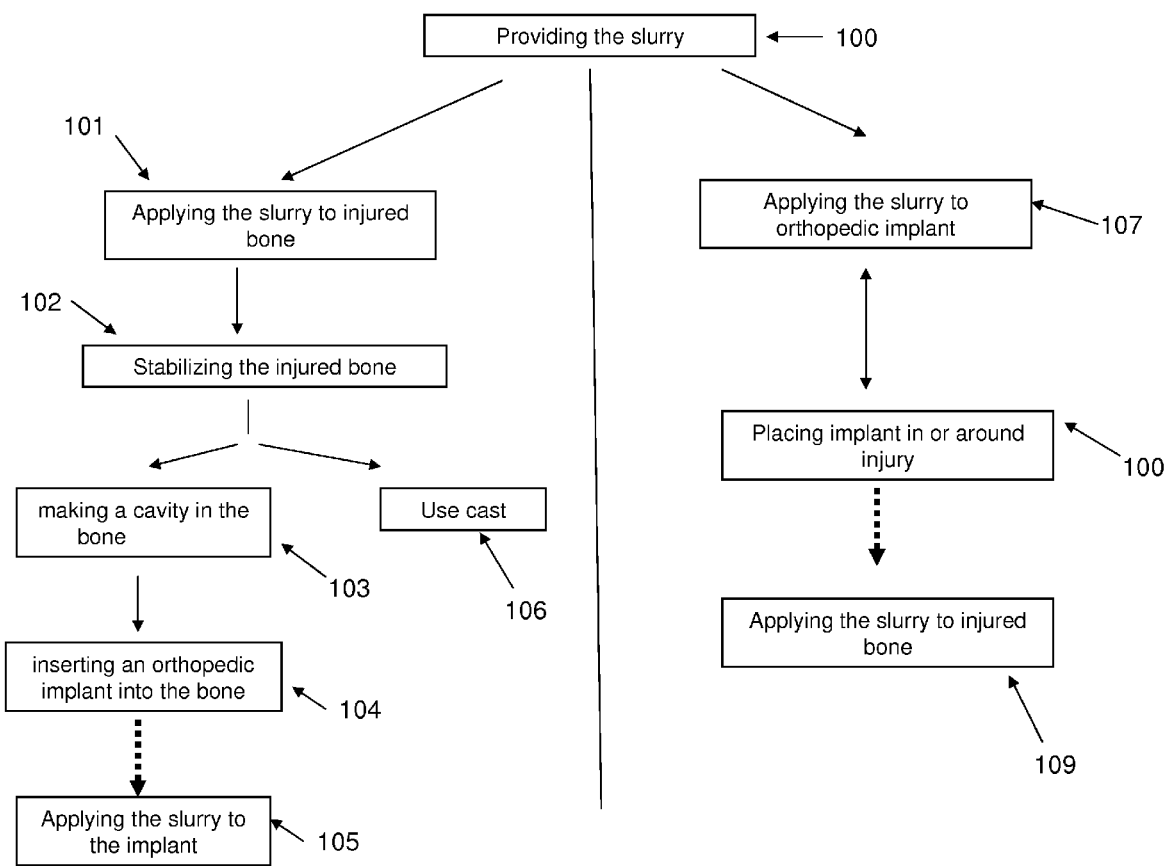

With reference to FIG. 5, after the slurry has been prepared, as indicated by step 100, the slurry can be applied to the site of the injury. In one embodiment, indicated in step 101, the slurry can be applied directly to the injured bone. Various application methods may be used to apply the slurry to the target site. For example, because certain embodiments of the composition are flowable but cohesive and compression resistant, the composition may be injected into the target site using a cannula or syringe of sufficient diameter and should thereafter remain at the target site, thus providing a minimally invasive treatment. In a subsequent step 102, the bone is then stabilized. One example of stabilizing the injured bone using an orthopedic implant is indicated in steps 103 and 104, and may include making a cavity in the bone and inserting the implant into the bone 104. In a subsequent step 105, the composition may then be applied to the implant if desired. In addition to using the orthopedic implant, other well known methods to stabilize the bone may be used, as indicated in step 106. For example, a fractured limb may be immobilized with a plaster or fiberglass cast, which holds the bones in position and immobilizes the joints above and below the fracture.

In another embodiment, indicated by step 107, the slurry is applied to an orthopedic implant using the applicator or by dipping the implant into the slurry. In step 108, the implant may then be placed in or around the injured area. Alternatively, the implant may be first placed in or around the injured area and then the slurry may be applied. The composition may also be applied to the implant both before and after the insertion. In addition to applying the composition to the implant, the composition may be applied directly to the injured area, as indicated by step 109.

All publications cited in the specification, both patent publications and non-patent publications, are indicative of the level of skill of those reasonably skilled in the art to which this invention pertains. All these publications are herein fully incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the following claims.

What is claimed is:

1. A composition for promoting bone formation comprising:
   an effective amount of a biological factor; and
   a flowable carrier slurry having a viscosity of about $1 \times 10^8$ centipoises and comprising a biocompatible fluid, a biodegradable polymer consisting of soluble collagen and insoluble collagen, a carbodiimide, and a calcium phosphate compound, the calcium phosphate compound being granules having average pore sizes of 0.1 to 25 microns and the granules having diameters of 100 to 1600 microns, wherein the volume ratio of the biocompatible fluid to the biodegradable polymer and calcium phosphate compound is between about 1:1 to 1:4 and the ratio of the biodegradable polymer to the calcium phosphate is between 75:25 and 50:50 by weight and the biological factor is released over 7 to 21 days and the calcium phosphate compound comprises 15% hydroxyapatite uniformly distributed through 85% beta-tricalcium phosphate.

2. The composition of claim 1 wherein the biological factor is selected from the group consisting of BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18, VEGF-A, VEGF-B, VEGF-C, VEGF-D, VEGF-E, CTGF-1, CTGF-2, CTGF-3, Osteoprotegerin, TGF-β-1, TGF-β-2, TGF-β-3, anti-TNFa, PDGF-A, PDGF-B, PDGF-C, PDGF-D, GDF-5, Statins, Nell-1 protein, LIM mineralization protein and peptides, IGF-I, IGF-II, FGF, BDGF II, recombinant versions thereof, and heterodimers thereof.

3. The composition of claim 1, wherein the biological factor is a bone morphogenetic protein (BMP).

4. The composition of claim 1, wherein the concentration of the biological factor in the composition is between about 0.01 to 10 mg of the biological factor per cc of the carrier slurry (mg/cc).

5. The composition of claim 1, wherein the amount of the composition is between approximately 7 and 12 cc and the composition is formed with between about 4 and 8 ml of the biocompatible fluid.

6. The composition of claim 5, wherein the concentration of the biological factor in the composition is between about 0.5 and 1.0 mg/cc.

7. The composition of claim 1, wherein the amount of the composition is between approximately 4 and 6 cc and the composition is formed with between about 2 and 4 ml of the biocompatible fluid.

8. The composition of claim 7, wherein the concentration of the biological factor in the composition is between about 0.10 and 0.3 mg/cc.

9. A medical kit for making a carrier slurry comprising:
   a biological factor;

a biodegradable polymer consisting of soluble and insoluble collagen;

a calcium phosphate compound, the calcium phosphate compound being granules having average pore sizes of 0.1 to 25 microns and diameters of 100 to 1600 microns;

a carbodiimide;

a biocompatible fluid; and an applicator, wherein the ratio of the biocompatible fluid to the biodegradable polymer and calcium phosphate compound is between about 1:1 to 1:4 and the ratio of biodegradable polymer to the calcium phosphate compound is between 75:25 and 50:50 by weight and the biological factor is capable of being released from the carrier slurry over 7 to 21 days and the slurry has a viscosity of about $1 \times 10^8$ centipoises and the calcium phosphate compound comprises 15% hydroxyapatite uniformly distributed through 85% beta-tricalcium phosphate.

10. The medical kit of claim 9, wherein the applicator is adapted for applying the biological factor and the carrier slurry resulting from hydrating the biodegradable polymer and the calcium phosphate compound with the biocompatible fluid to a site of bone repair or to an orthopedic implant.

11. The medical kit of claim 9, wherein the biological factor and the biocompatible fluid are contained in separate containers.

12. The medical kit of claim 9, wherein the biological factor is pre-dissolved in the biocompatible fluid.

13. The kit of claim 9, wherein the biocompatible fluid is selected from a group consisting of water, saline solution, buffered solutions, blood, bone marrow aspirant, and glycerol.

14. The kit of claim 9, wherein the biological factor is selected from the group consisting of BMP-2, BMP-3, BMP-4, BMP-5, BMP-6, BMP-7, BMP-8, BMP-9, BMP-10, BMP-11, BMP-12, BMP-13, BMP-15, BMP-16, BMP-17, BMP-18, VEGF-A, VEGF-B, VEGF-C, VEGF-D, VEGF-E, CTGF-1, CTGF-2, CTGF-3, Osteoprotegerin, TGF-β-1, TGF-β-2, TGF-β-3, anti-TNF-α, PDGF-A, PDGF-B, PDGF-C, PDGF-D, GDF-5, statins, Nell-1 protein, LIM mineralization protein and peptides, IGF-I, IGF-II, FGF, BDGF II, recombinant versions thereof, and heterodimers thereof.

15. The kit of claim 9, wherein the biological factor is a bone morphogenetic protein (BMP).

16. The kit of claim 9, wherein the kit contains approximately 2 to 4 ml of the biocompatible fluid.

17. The kit of claim 16, wherein the kit contains between about 0.8 and 1.2 mg of the biological factor.

18. The kit of claim 17, wherein the kit forms between 4 and 6 cc of the carrier slurry.

19. The kit of claim 9, wherein the kit contains approximately 4 to 8 ml of the biocompatible fluid.

20. The kit of claim 19, wherein the kit contains between about 3 and 6 mg of the biological factor.

21. The kit of claim 20, wherein the kit forms between about 7 and 12 cc of the slurry.

22. The kit of claim 9, wherein the biodegradable polymer and the calcium phosphate particles are pre-mixed.

23. The kit of claim 9, wherein the biodegradable polymer and the calcium phosphate particles are provided in separate containers.

24. The kit of claim 9 further comprising a spatula, a connector or a set of instructions.

25. A slurry for applying to bone or an orthopedic implant, the slurry consisting of an effective amount of a BMP-2, a biocompatible fluid, a carbodiimide, biodegradable polymer consisting of insoluble bovine collagen and soluble bovine collagen and a biphasic calcium phosphate, the biphasic calcium phosphate being granules having average pore sizes of 0.1 to 25 microns and diameters of 100 to 1600 microns, wherein the volume ratio of the biocompatible fluid to the biodegradable collagen and the biphasic calcium phosphate of the slurry is between about 1:1 to 1:4 and the slurry remains flowable for 7 to 30 days and the ratio of the biodegradable polymer to the biphasic calcium phosphate is between 75:25 and 50:50 by weight and the biological factor is released over 7 to 21 days and wherein the slurry has a viscosity of about $1 \times 10^8$ centipoises and the biphasic calcium phosphate comprises 15% hydroxyapatite uniformly distributed through 85% beta-tricalcium phosphate.

26. A slurry according to claim 25, wherein the slurry has a residence time in the body of 7 to 30 days when applied to the bone or the orthopedic implant and the collagen consists of insoluble collagen and soluble collagen in the slurry at a weight ratio between about 30:70 and about 70:30.

* * * * *

UNITED STATES PATENT AND TRADEMARK OFFICE
CERTIFICATE OF CORRECTION

| | | |
|---|---|---|
| PATENT NO. | : 8,048,857 B2 | Page 1 of 1 |
| APPLICATION NO. | : 11/612853 | |
| DATED | : November 1, 2011 | |
| INVENTOR(S) | : McKay et al. | |

It is certified that error appears in the above-identified patent and that said Letters Patent is hereby corrected as shown below:

In Column 2, Lines 3-4, delete "a intraopertive" and insert -- an intraoperative --, therefor.

In Column 4, Line 66, delete "polyactic-glycolic" and insert -- polylactic-glycolic --, therefor.

In Column 8, Line 42, in Claim 2, delete "anti-TNFa," and insert -- anti-TNF-α, --, therefor.

Signed and Sealed this
Twenty-ninth Day of November, 2011

David J. Kappos
*Director of the United States Patent and Trademark Office*